United States Patent

Murthy et al.

Patent Number: 5,750,714
Date of Patent: May 12, 1998

[54] PROCESS FOR THE MANUFACTURE OF RELATED INTERMEDIATES INCLUDING CISTOFUR

[75] Inventors: K.S. Keshava Murthy; Gamini Weeratunga; Bruno Konrad Radatus; Kanwar Pal Singh Sidhu, all of Brantford, Canada

[73] Assignee: Brantford Chemicals Inc., Brantford, Canada

[21] Appl. No.: 571,653

[22] Filed: Dec. 13, 1995

[51] Int. Cl.$^6$ ............................................. C07D 277/28
[52] U.S. Cl. ...................... 548/205; 548/340.1; 549/495
[58] Field of Search .............................. 548/205, 340.1; 549/495

[56] References Cited

U.S. PATENT DOCUMENTS

| | | | |
|---|---|---|---|
| 4,221,802 | 9/1980 | Durant | 424/273 |
| 4,242,517 | 12/1980 | Dockner | 548/342 |
| 4,471,122 | 9/1984 | Crenshaw | 546/209 |

*Primary Examiner*—Robert Gerstl
*Attorney, Agent, or Firm*—Ivor M. Hughes; Neil H. Hughes; Marcelo K. Sarkis

[57] ABSTRACT

A process of manufacture of:

$$R-CH_2-S-CH_2-CH_2-NH_2 2HCl$$

wherein R is selected from the group consisting of

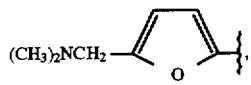 (a)

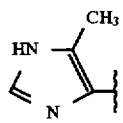

(b)

and

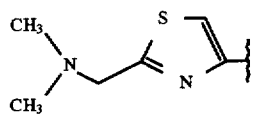 (c)

is provided, the said process comprising reacting $R-CH_2OH \cdot HCl$ with $HSCH_2CH_2NH_2 \cdot HCl$ in a suitable solvent in the presence of an effective amount of Hydrochloric acid.

18 Claims, No Drawings

PROCESS FOR THE MANUFACTURE OF RELATED INTERMEDIATES INCLUDING CISTOFUR

FIELD OF INVENTION

This invention relates to a new process for the manufacture of Cistofur Dihydrochloride. This compound is suitable for use as an intermediate for the manufacture of the anti-ulcer drug, Ranitidine and its hydrochloride form.

This invention also has broader application and can be used to manufacture suitable other intermediates for the manufacture of such medicines such as Cimetidine and Nizatidine.

BACKGROUND OF THE INVENTION

Ranitidine may be manufactured using the intermediate Cistofur [(2-[[[5-(dimethylamino)methyl-2-furanyl]methyl]thio]-ethanamine)]. This intermediate (free base) has also been made in its mono and dihydrochloride forms and used in the manufacture of Ranitidine (free base) and Ranitidine hydrochloride form.

Canadian Letters Patent 1 099 268 purports to teach the preparation of 2-[[[5-(dimethylamino)methyl-2-furanyl]methyl]thio]-ethanamine (Cistofur base) at page 25 Example A. 5-Dimethylaminomethyl-2-furfuryl alcohol (Furamine base) is reacted with cysteamine hydrochloride (equivalent) in concentrated hydrochloric acid at 0° C. for 18 hours. The mixture was then neutralized with sodium carbonate, extracted with diethyl ether, the diethyl ether removed and the residue distilled at reduced pressure to yield the Cistofur base. The disadvantages of this procedure for industrial use are:

1) a large amount of hydrochloric acid has to be neutralized;
2) the difficulties associated with extracting a solid-liquid mixture with an organic solvent;
3) the need to remove the extracting solvent which is diethyl ether (a fire hazard);
4) the need to distill the product under high vacuum (1 mm Hg) conditions; and,
5) the resultant base must be used as quickly as possible since it degrades on storage.

Canadian Letters Patent 1,279,328 purports to overcome some of the above disadvantages by teaching how to prepare Cistofur dihydrochloride and Cistofur monohydrochloride. Cistofur dihydrochloride was purported to have been prepared by reacting the hydrochloride of 5-(dimethylamino)methyl-2-furfuryl alcohol (Formula I of the Patent) with cysteamine hydrochloride (Formula II of the Patent) in the presence of a catalytic amount of mineral acid (e.g. hydrochloric acid, phosphoric acid) (melt or fusion at 20° C. to 120° C. in the absence of any solvent).

Optionally an organic acid (having a pka value of 0 to 2, such as p-toluene sulfonic acid) can be used or a catalytic amount of a substance which furnishes under the above mentioned conditions a mineral acid (e.g. aluminum chloride) or an organic acid (e.g. p-toluene sulphonic acid) having a pka value of 0 to 2. Optionally an inert organic diluent [benzene, dichloroethane, petroleum ether) which does not dissolve the reactants (pseudo-melt conditions) can also be used.

The product can be isolated by adding a lower alcohol (e.g. ethanol) or a mixture of a lower alcohol (ethanol) and a lower aliphatic ketone (e.g. acetone) to produce a precipitate which is filtered, washed with the same solvent and dried to yield the desired Cistofur dihydrochloride in good yield (72–92%).

This process, however, suffers a substantial number of disadvantages if this process is to be used on an industrial scale including:

1. fusion is not the preferred route of synthesis especially in large scale;
2. a mixed solvent system (ethanol, acetone) used to precipitate the product from the reaction mixture makes the recovery of each of the solvents difficult; and,
3. purification of the resultant product requires more processing than is desirable.

It is therefore an object of this invention to provide an improved process for the manufacture of Cistofur dihydrochloride which results in a highly pure product without the need for recrystallisation prior to use.

It is a further object of this invention to provide such process which is capable of being used to produce commercial quantities of Cistofur Dihydrochloride (suitable for use in the commercial manufacture of Ranitidine free base and/or hydrochloride form) at reduced cost.

It is still a further object of this invention to provide processes which are capable of making commercial quantities of other intermediates for use to manufacture medicines such as Cimetidine and Nizatidine.

Further and other objects of the invention will be realized by those skilled in the art from the following Summary of Invention and Detailed Description of Embodiments thereof.

SUMMARY OF THE INVENTION

According to one aspect of the invention a process of manufacture of

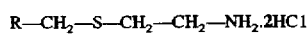

is provided wherein R is selected from

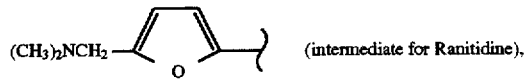 (intermediate for Ranitidine),

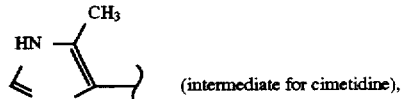 (intermediate for cimetidine),

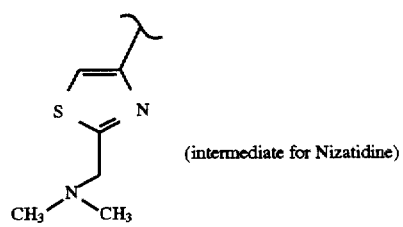 (intermediate for Nizatidine)

in which R—CH$_2$OH.HCl is reacted with HSCH$_2$CH$_2$NH$_2$.HCl in a solvent (for example an alkanol, preferably isopropanol which is preferred) in the presence of Hydrochloric acid.

The starting materials are known and may be made by methods known to persons skilled in the art or may be purchased where available.

Thus according to an aspect of the invention a process is provided comprising reacting:

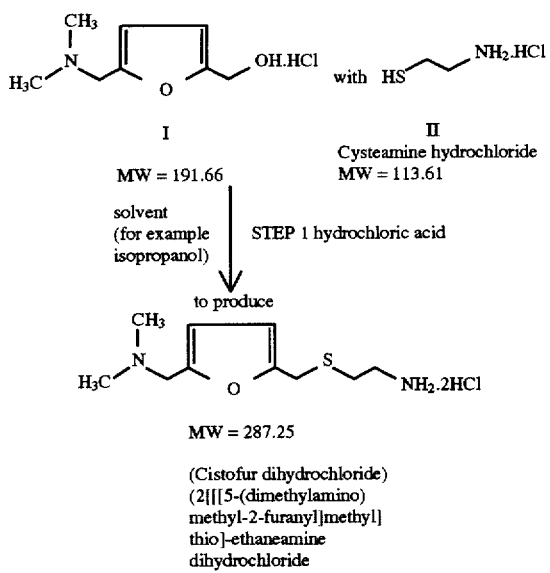

MW = 191.66    II Cysteamine hydrochloride MW = 113.61

I solvent (for example isopropanol)    STEP 1 hydrochloric acid to produce

MW = 287.25

(Cistofur dihydrochloride)
(2[[[5-(dimethylamino)
methyl-2-furanyl]methyl]
thio]-ethaneamine
dihydrochloride According to another aspect of the invention, the following process is provided:

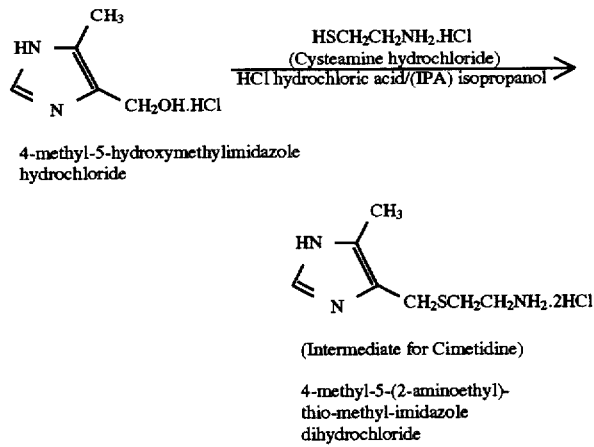

4-methyl-5-hydroxymethylimidazole hydrochloride (Intermediate for Cimetidine)

4-methyl-5-(2-aminoethyl)-thio-methyl-imidazole dihydrochloride

According to another aspect of the invention, the following process is provided:

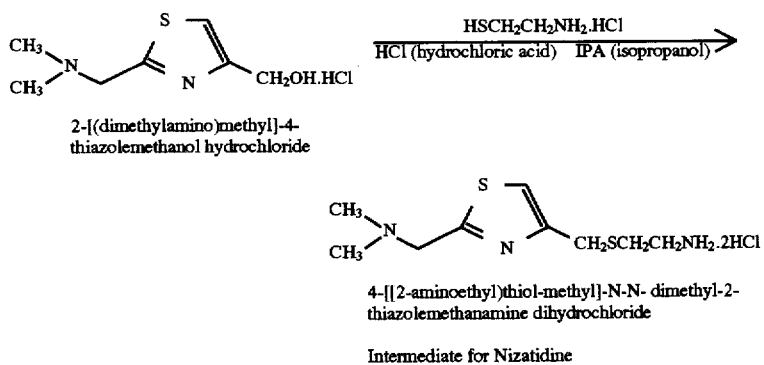

2-[(dimethylamino)methyl]-4-thiazolemethanol hydrochloride

4-[[2-aminoethyl)thiol-methyl]-N-N- dimethyl-2-thiazolemethanamine dihydrochloride Intermediate for Nizatidine The Hydrochloric Acid may be present in an embodiment as aqueous hydrochloric acid or in another embodiment, as isopropanolic hydrochloric acid (which may be prepared by bubbling HCl gas through isopropanol until the desired concentration or percentage concentration is achieved). Preferred amounts of HCl used is about 0.5 molar equivalents with respect to starting materials. However, the amount may be varied over a broad range for example, an amount of 0.1 molar equivalent. The resultant product is subsequently precipitated.

Where isopropanol is the solvent, the precipitation can be efficiently carried out by the addition of more isopropanol, preferably also by the addition of small amounts of water. (Where the solvent is for example an alkanol other than isopropanol (such as ethanol, butanol, or pentanol, etc.) precipitation may be more cumbersome.)

The solution is preferably heated to Temperatures in the order of 40° C.–90° C.

The invention will now be illustrated with respect to the following Detailed Description of some embodiments of the invention.

Preparation of 2-[(2-aminoethyl)-thiomethyl]-5-dimethylaminomethylfuran dihydrochloride

EXAMPLE 1

A mixture containing cysteamine hydrochloride (37.5 g, 0.33 mol), 5-dimethylaminomethyl-2-furfuryl alcohol hydrochloride (64.6 g, 0.337 mol), concentrated hydrochloric acid (16 mL) and isopropanol (32 mL) is heated to 75°–80° C. for 3h. Isopropanol (508 mL) and water (9 mL) are added and the reaction mixture is heated to 65°–70° C. for 1 h. The mixture is stirred at ambient temperature for 10 to 16 hours. The precipitate is filtered, washed with more isopropanol and dried to give 71 g (75%) of the aimed product. HPLC purity greater than 99.5%.

EXAMPLE 2

A mixture containing cysteamine hydrochloride (37.5 g 0.33 mol), 5-dimethylaminomethyl-2-furfuryl alcohol hydrochloride (64.6 g, 0.337 mol), isopropanolic hydrochloric acid (23 mL) and isopropanol (32 mL) is heated to 75°–80° C. for 3 h. Isopropanol (400 mL) and water (18 mL) are added and the reaction mixture is heated to 65°–70° C. and maintained until total dissolution is achieved. The mixture is stirred at ambient temperature for 10 to 16 hours, the precipitate is filtered and washed with more isopropanol and dried to give 67.4 g (71%) of the aimed product.

EXAMPLE 3

A mixture containing cysteamine hydrochloride (29.5 g, 0.26 mol), 5-dimethylaminomethyl-2-furfuryl alcohol hydrochloride (50 g, 0.26 mol), isopropanolic hydrochloric acid (40 mL) and isopropanol (11 mL) is heated to 50°–55° C. for 15–18 hours. Isopropanol (400 mL) is added to the mixture and heated at 70°–80° C. for 2 hours. Then it is cooled to room temperature for 10–12 hours. The precipitate is filtered and washed with isopropanol and dried to give 58 g (78%) of the expected product.

Embodiments of our process thus overcome the previously mentioned disadvantages discussed by reacting furamine hydrochloride with cysteamine hydrochloride dissolved in a mixture of isopropanol and hydrogen chloride gas or isopropanol and concentrated aqueous hydrochloric acid at a temperature of 70°–80° C. for 3–4 hours. The product is precipitated preferably by adding the solvent isopropanol and water to obtain product of the highest purity on that event the final water content in the mixture from which the product is precipitated is about 5–10% with respect to the isopropanol. The product thus obtained is Cistofur dihydrochloride with HPLC purity greater than 99.0% and often greater than 99.5% in yields of 70–80%. Some of the advantages of the above processes which comprise embodiments of the invention are:

1) Analytical grade Cistofur dihydrochloride is obtained directly without recrystallization.
2) High yields are obtained using substantially a single solvent which solvent can be recovered using available azeotrope distillation technology.
3) Reaction and precipitation are done in the same reactor.
4) The process is easily used for the manufacture of commercial batches.

EXAMPLE 4

Preparation of 4-methyl-5-(2-aminoethyl)-thiomethylimidazole dihydrochloride

A mixture containing cysteamine hydrochloride (18.75 g, 0.165 mol),-4-hydroxymethyl-5-methylimidazole hydrochloride (25 g, 0.169 mol), concentrated hydrochloric acid (10 mL) and isopropanol (17 mL) is heated to 70°–80° C. The solvent is removed under reduced pressure and the crude product is pulped with n-butanol. The precipitate is filtered and dried to give 19.7 g of the expected product (49%).

EXAMPLE 5

In like manner, 4-[[2-aminoethyl)thio]-methyl-N-N-dimethyl-2-thiazolemethanamine dihydrochloride may be prepared as follows:

A mixture containing cysteamine hydrochloride (37.5 g, 0.33 mol), 2-[(dimethylamino)methyl]-4-thiazolemethanol hydrochloride (68.8 g, 0.33 mol), concentrated hydrochloric acid (16 mL) and isopropanol (32 mL) may be heated to 75°–80° C. for 6–10 hours. The solvent may then be removed and the product recrystallized from suitable solvent preferably isopropanol/water to give aimed product.

As many changes can be made to the examples (for example changing of solvent) without departing from the scope of the invention, it is intended that all material contained herein be interpreted as illustrative of the invention and not in a limiting sense. For example while isopropanol is the preferred solvent and also enables the precipitation of for example the Cistofur dihydrochloride therefrom, isopropanol would not be the only suitable solvent. Persons skilled in the art would appreciate that other solvents are useful such as alkanols in sufficient amounts.

The embodiments of the Invention in which an exclusive property or privilege is claimed are as follows:

1. A process of manufacture of

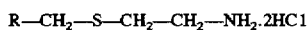

wherein R is selected from the group consisting of

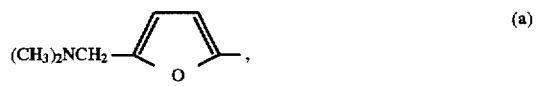

and

is provided, the said process comprising reacting R—CH$_2$OH.HCL with HSCH$_2$CH$_2$NH$_2$HCl in a suitable solvent selected from the group consisting of an alkanol in the presence of an effective amount of Hydrochloric acid.

2. The process of claim 1 wherein the alkanol is isopropanol.

3. The process of claim 1 wherein R is

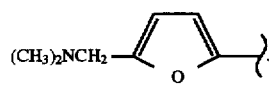

4. The process of claim 2 wherein R is

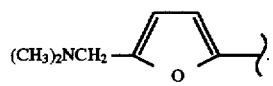

5. The process of claim 1 wherein R is

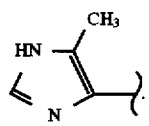

6. The process of claim 2 wherein R is

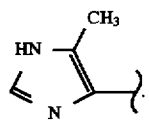

7. The process of claim 1 wherein R is

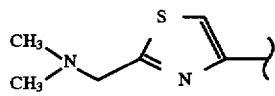

8. The process of claim 2 wherein R is

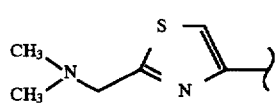

9. The process of reacting:

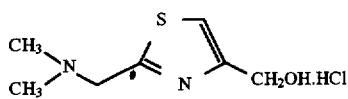

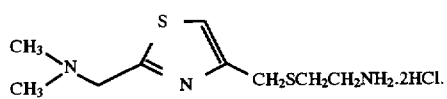

10. The process of claim 1 or 2 wherein the Hydrochloric Acid is present as aqueous hydrochloric acid or isopropanolic hydrochloric acid.

11. The process of claim 3 or 4 wherein the Hydrochloric Acid is present as aqueous hydrochloric acid or isopropanolic hydrochloric acid.

12. The process of claim 5 or 6 wherein the Hydrochloric Acid is present as aqueous hydrochloric acid or isopropanolic hydrochloric acid.

13. The process of claim 7 or 8 wherein the Hydrochloric Acid is present as aqueous hydrochloric acid or isopropanolic hydrochloric acid.

14. The process of claim 1 or 2 further comprising the step of precipitating the desired product.

15. The process of claim 2 further comprising the step of precipitating the desired product by the addition of more isopropanol and water.

16. The process of claim 1 or 2 further comprising the step of precipitating the desired product by the addition of more solvent and water.

17. The process of claim 1 or 2 wherein the solution is heated to Temperatures in the order of 40° C.–90° C.

18. The process of claim 3 or 4 wherein the solution is heated to Temperatures in the order of 40° C.–90° C.

* * * * *

UNITED STATES PATENT AND TRADEMARK OFFICE
CERTIFICATE OF CORRECTION

PATENT NO. : 5,750,714
DATED : May 12, 1998
INVENTOR(S) : K.S. Keshava Murthy, Gamini Weeratunga, Bruno Konrad Radatus and Kanwar Pal Singh Sidhu It is certified that error appears in the above-identified patent and that said Letters Patent is hereby corrected as shown below:

In Claim 9 of the Patent at column 7, line 6, the following phrase should be inserted between the compounds:

--- with $HSCH_2CH_2NH_2 \cdot HCl$ in a suitable solvent in the presence of an effective amount of hydrochloric acid to produce ---

Signed and Sealed this

Twenty-ninth Day of September, 1998

Attest:

BRUCE LEHMAN

Attesting Officer

Commissioner of Patents and Trademarks